US008829203B2

(12) United States Patent  (10) Patent No.: US 8,829,203 B2
Meijer et al.  (45) Date of Patent: Sep. 9, 2014

(54) 3',6-SUBSTITUTED INDIRUBINS AND THEIR BIOLOGICAL APPLICATIONS

(75) Inventors: Laurent Meijer, Roscoff (FR);
Leandros Skaltsounis, Athens (GR);
Emmanuel Mikros, Ag. Paraskevi (GR);
Prokopios Magiatis, Ambelakia (GR);
Carl Johnson, Nashville, TN (US)

(73) Assignee: Centre National de la Recherche Scientifique (CNRS), Paris Cedex (FR)

( * ) Notice: Subject to any disclaimer, the term of this patent is extended or adjusted under 35 U.S.C. 154(b) by 270 days.

(21) Appl. No.: 12/737,640

(22) PCT Filed: Jul. 21, 2009

(86) PCT No.: PCT/IB2009/053153
§ 371 (c)(1),
(2), (4) Date: Feb. 1, 2011

(87) PCT Pub. No.: WO2010/013168
PCT Pub. Date: Feb. 4, 2010

(65) Prior Publication Data
US 2011/0136808 A1    Jun. 9, 2011

Related U.S. Application Data

(60) Provisional application No. 61/085,432, filed on Aug. 1, 2008.

(30) Foreign Application Priority Data

Aug. 1, 2008 (EP) .................. 08161646

(51) Int. Cl.
C09B 7/04    (2006.01)
(52) U.S. Cl.
USPC ......................................... 548/459
(58) Field of Classification Search
USPC ......................................... 548/459
See application file for complete search history.

(56) References Cited

U.S. PATENT DOCUMENTS

| 6,987,092 | B1 | 1/2006 | Eisenbrand et al. |
| 2007/0276025 | A1 | 11/2007 | Meijer |
| 2010/0331327 | A1 | 12/2010 | Meijer et al. |
| 2011/0136808 | A1 | 6/2011 | Meijer et al. |

FOREIGN PATENT DOCUMENTS

WO    2005/041954    5/2005

OTHER PUBLICATIONS

Ferandin, et al. Document No. 145:271522 (2006), retrieved from CAPLUS.*
Olivier, et al. Document No. 150:162202 (2008), retrieved from CAPLUS.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Polychronopoulos et al., "Structural bases for the synthesis of Indirubins as potent and selective inhibitors of glycogen synthase kinase-3 and cyclin dependent kinases", Journal of Medicinal Chemistry, vol. 47, 2004, pp. 935-946, XP002453468.
Meijer et al., "GSK-3-Selective inhibitors derived from Tyrian Purple Indirubins", Chemistry & Biology, vol. 10, 2003, pp. 1255-1266, XP002453469.
Ribas et al, "7-Bromindirubin-3'-oxime induces capase-independent cell death", Oncogene, vol. 25, No. 47, 2006, pp. 6304-6318, XP002453470.
Ferandin et al., "3'-Substituted 7-Halogenoindirubins, a New Class of Cell Death Inducing Agents", Journal of Medicinal Chemistry, vol. 49, No. 15, 2006, pp. 4638-4649, XP002453471.
International Search Report for PCT/IB2006/004152, mailed Oct. 23, 2007.
International Search Report for PCT/IB2009/053153, mailed Sep. 24, 2009.
K. Vougogiannopoulou et al., "Soluble 3', 6-substituted Indirubins with Enchanced Selectivity towards Glycogen Synthase Kinase-3 Alter Circadian Period", J. Med. Chem., vol. 51, No. 20, Sep. 25, 2008, pp. 6421-6431.

* cited by examiner

Primary Examiner — Shawquia Young
(74) Attorney, Agent, or Firm — Nixon & Vanderhye P.C.

(57) ABSTRACT

Indirubin derivatives of formula (I) wherein R represents $-(A)_n-R^1$ or $-CO-N(R^2,R^3)$ with •A being C1-C5 alkylene group, optionally substituted by one or several $A^1$ radical, $A^1$ being an halogen Br, OH, $OR^4$ or $NH_2$, $R^4$ being C1-C5 alkyl; $-R^1$ being halogen, OH, $N(R^2, R^3)$; $R^2$ and $R^3$, identical or different, being C1-C5 alkyl, optionally substituted by $A^1$ such as above defined, or $R^2$ and $R^3$ are part of a cycle with 5 or 6 elements optionally comprising another heteroatom such as O or N; •n=1–5. It also relates to the biological application thereof.

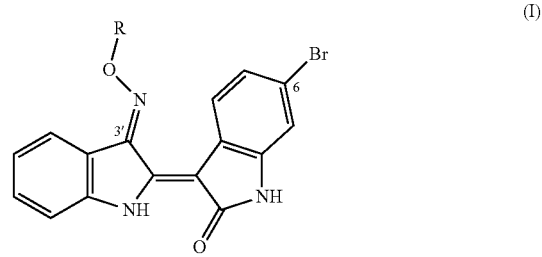

9 Claims, 4 Drawing Sheets

3',6-SUBSTITUTED INDIRUBINS AND THEIR BIOLOGICAL APPLICATIONS

This application is the U.S. national phase of International Application No. PCT/IB2009/053153, filed 21 Jul. 2009, which designated the U.S. and claims priority to European Application No. 08161646.8, filed 1 Aug. 2008 and U.S. Provisional Application No. 61/085,432, filed 1 Aug. 2008, the entire contents of each of which are hereby incorporated by reference.

The invention relates to 3',6-substituted indirubins with enhanced selectivity towards glycogen synthase kinase-3 (GSK-3). It also relates to their biological applications.

Among the 518 protein kinases which constitute the human kinome, GSK-3 stand out as a particularly interesting and well-studied family of serine/threonine kinases. There are only two GSK-3 forms (GSK-3α, and GSK-3β), which share extensive similarity (84% overall identity, 98% within the catalytic domain), the main difference coming from an extra Gly-rich stretch in the N terminal domain of GSK-3α. GSK-3 are highly conserved protein kinases present from unicellular parasites to yeast up to mammals. These kinases are involved in numerous critical physiological events such as Wnt and Hedgehog signaling, embryonic development (pattern specification and axial orientation), transcription, insulin action, cell division cycle, cell death, cell survival, differentiation, multiple neuronal functions, circadian rhythm regulation, stem cell differentiation, etc. . . . In addition GSK-3 are implicated in a large diversity of human diseases, including nervous system disorders such as Alzheimer's disease, schizophrenia, bipolar disorder, diabetes, heart hypertrophy, renal diseases, shock and inflammation, cancers, etc. . . . There is thus a strong rationale supporting the search for potent and selective GSK-3 inhibitors for their use as pharmacological tools in basic research, as potential drugs for the treatment of specific diseases and for the maintenance of pluripotent stem cells in the absence of feeder cells. Numerous GSK-3 inhibitory scaffolds have been described. Interestingly many of these inhibitors also interact with cyclin-dependent kinases (CDKs), another family of well-studied key regulatory enzymes.

Among GSK-3 inhibitors, derivatives of the bis-indole indirubin (collectively referred to as indirubins) appear as a class of original and promising tools and agents. Their moderate selectivity might be an inconvenient when used as a research reagent, but their combined effects on several disease-relevant targets (in particular CDKs and GSK-3) may constitute an advantage for potential therapeutic applications. Among many indirubins, 6-bromo-indirubin-3'-oxime (6BIO) [1-3] has been widely used to investigate the physiological role of GSK-3 in various cellular settings and to alter the fate of embryonic stem cells[1].

While highly potent and relatively selective kinase inhibitory indirubins have been developed, they usually exhibit low water solubility. To address the solubility problem of these promising compounds, the inventors have designed novel analogues of 6BIO with increased hydrophilicity. Improvement of the hydrophilic character of a molecule may be approached by several ways. The decrease of the aromatic character of indirubin scaffold by changing the hybridization state of an aromatic carbon atom to sp3 has been proposed as a way to enhance solubility. An alternative method is the introduction of hydrophilic groups on the molecule. Obviously, it is essential that the optimization of hydrophilicity does not negatively impact on either the potency or on the selectivity of the molecule towards the target kinase. The choice of the substitution position is thus highly significant since there are two important areas of the molecule that cannot be altered without dramatic decrease of efficacy on kinases. The first one is the pharmacophore consisting of the lactam nitrogen and carbonyl and the heterocyclic nitrogen of the bis-indole core that form the key hydrogen bonding interaction pattern with the active site of the kinase targets. The second is the bromine substitution at position 6 which is the selectivity determinant of 6BIO towards GSK-3β. A detailed analysis of the crystal structure of GSK-3β in complex with 6BIO was carried out by the inventors. On the basis of the information thus obtained, they considered that the 3' position was critical for carrying out chemical modifications on the indirubin scaffold. They thus designed and synthesized a series of 6-bromo-indirubins with various substitutions on position 3'. Unexpectedly, these molecules displayed high potency towards GSK-3, enhanced selectivity and much increased water-solubility. These molecules were evaluated for their GSK-3 inhibitory actions in several cellular systems.

An object of the invention is then to provide new 3',6-substituted indirubins having enhanced selectivity towards GSK-3.

Another object of the invention is to provide a method for obtaining said indirubins.

According to still another object, the invention aims to provide pharmaceutical compositions and biological reagents containing said indirubins as active principles as well as a method of treating pathologies associated with GSK-3 deregulations comprising the use of such active principles.

The indirubin derivatives of the invention have formula (I)

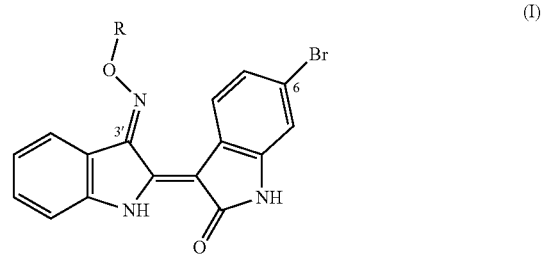

(I)

wherein
R represents -(A)$_n$- R$^1$ or —CO—N(R$^2$,R$^3$) with
  A being C1-C5 alkylene group, optionally substituted by one or several A$^1$ radical, A$^1$ being halogen Br, OH, OR$^4$ or NH$_2$, R$^4$ being a C1-C5 alkyl;
  R$^1$ being halogen, OH, N(R$^2$, R$^3$); R$^2$ and R$^3$, identical or different, being C1-C5 alkyl, optionally substituted by A$^1$ such as above defined, or R$^2$ and R$^3$ are part of a cycle with 5 or 6 elements, optionally comprising another heteroatom such as O or N;
  n=1-5.

The invention also relates to the pharmaceutically acceptable salts of the above defined derivatives. These salts comprise, inter alia, the chlorides, acetates, succinates, citrates of the above disclosed indirubins.

In a first family,
  R represents -(A)$_n$- R$^1$, with R$^1$ being halogen, OH, N(R$^2$, R$^3$) and R$^2$ and R$^3$, identical or different, are C1-C5 alkyl, optionally substituted by A$^1$ such as above defined.
  In a preferred group of said family, R$^1$ is halogen or OH. In advantageous derivatives of said group, A represents —(CH$_2$)$_{m1}$—CH(R$^1$)—(CH$_2$)$_{m2}$ radical, wherein m1=1-3 and m2 =0, 1-3.

In another preferred group of said family, $R^1$ is N ($R^2$, $R^3$).

According to a first embodiment, $R^2$ and $R^3$, identical or different, are C1-C5 alkyl, optionally substituted by $A^1$ such as above defined.

According to a second embodiment, $R^2$ and $R^3$ are part of a pyrrol, morpholinyl, piperazinyl radical, said radical being optionally substituted by one or several A1 and the piperazinyl radical being optionally substituted on the nitrogen at position by a C1-C5 alkyl, which can in turn be substituted by A1 such as above defined.

In advantageous derivatives of said groups, A is C1-C5 alkylene group.

In a second family,

R represents —CO—N($R^2$,$R^3$), with $R^2$ and $R^3$, identical or different, being a C1-C5 alkyl radical.

According to the invention, the synthesis of the above defined indirubin derivatives with $R^1$ being —N($R^2$, $R^3$) is advantageously based on the reaction of an oxime derivative of formula II

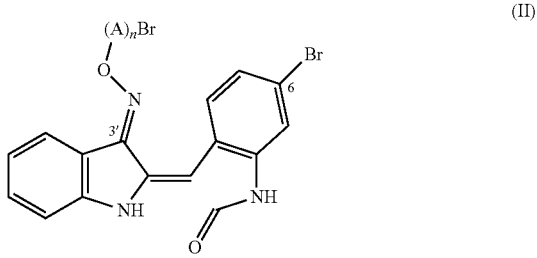

with an appropriate amine of formula III:

wherein,

A2 is a C1-C5 alkyl and R2 and R3 are as above defined.

Appropriate amines comprise pyrrolidine, morpholine, piperazine, N-methylpiperazine, hydroxyethylpiperazine, methoxyethylpiperazine, dimethylamine and diethylamine, N,N-bis-2-hydroxyethylamine, N-2,3-dihydroxypropyl-N-methyl amine, and N-2-hydroxyethoxyethyl piperazine.

The oxime derivative of formula II is advantageously prepared by the reaction of 6BIO with 1,2-dibromoethane in DMF and triethylamine $Et_3N$ at room temperature.

In addition, the carbamate derivatives wherein R represents a CO—N(R2, R3) radical are prepared by the reaction of 6BIO with N,N-dialkylcarbamyl chloride. The alcohols derivatives of formula I wherein A 1 is OH are prepared by the reaction of 6BIO with the appropriate 1,2-dibromoalcane or bromo alcohol. Indirubin and 6BIO were synthesized as previously reported[2].

Advantageously, said derivatives are less cytotoxic than the parent 6BIO compound, and demonstrated potent GSK-3 inhibition in cellular models. The invention thus provides means of great interest to treat pathologies associated with GSK3 deregulations such as Alzheimer's disease, diabetes, heart hypertrophy, in the field of embryonic stem cell pluripotency maintenance or the alteration of the circadian period in mammalians.

These results open new directions towards the design of pharmacologically favorable indirubins with development against such pathologies.

The invention thus relates to the new derivatives of formula I for use as drugs.

The invention then also concerns pharmaceutical compositions comprising therapeutically effective amount of at least one derivative of formula I or the pharmaceutically acceptable salts thereof, such as above defined, in association with a pharmaceutically acceptable vehicle.

During the production of the drugs, the active ingredients, used in therapeutically effective amounts are mixed with the pharmaceutically acceptable vehicles for the mode of administration chosen. These vehicles may be solids or liquids or gels.

The drugs may be under a form suitable for an administration preferably by intravenous route, but also by oral or injectable route intramuscular and subcutaneous routes, or nasal route.

Thus, for administration by the oral route, the medicaments may be prepared in the form of gelatin capsules, tablets, sugar-coated tablets, capsules, pills and the like. Such medicaments may contain from 10 micrograms to 1 g of active ingredient per unit.

For administration by injection (bolus or perfusion; intravenous, subcutaneous, intraperitoneal, intratechal, intradermous), the medicaments are provided in the form of sterile or sterilizable solutions.

They may also be in the form of emulsions or suspensions.

The doses per dosage unit may vary for example from 1 micrograms to 1 g of active ingredient.

Other characteristics and advantages of the invention are given in the following examples and with reference to FIGS. 1 to 3 which represent, respectively:

EXPERIMENTAL SECTION

Chemistry

General Chemistry Experimental Procedures

Figure 1:
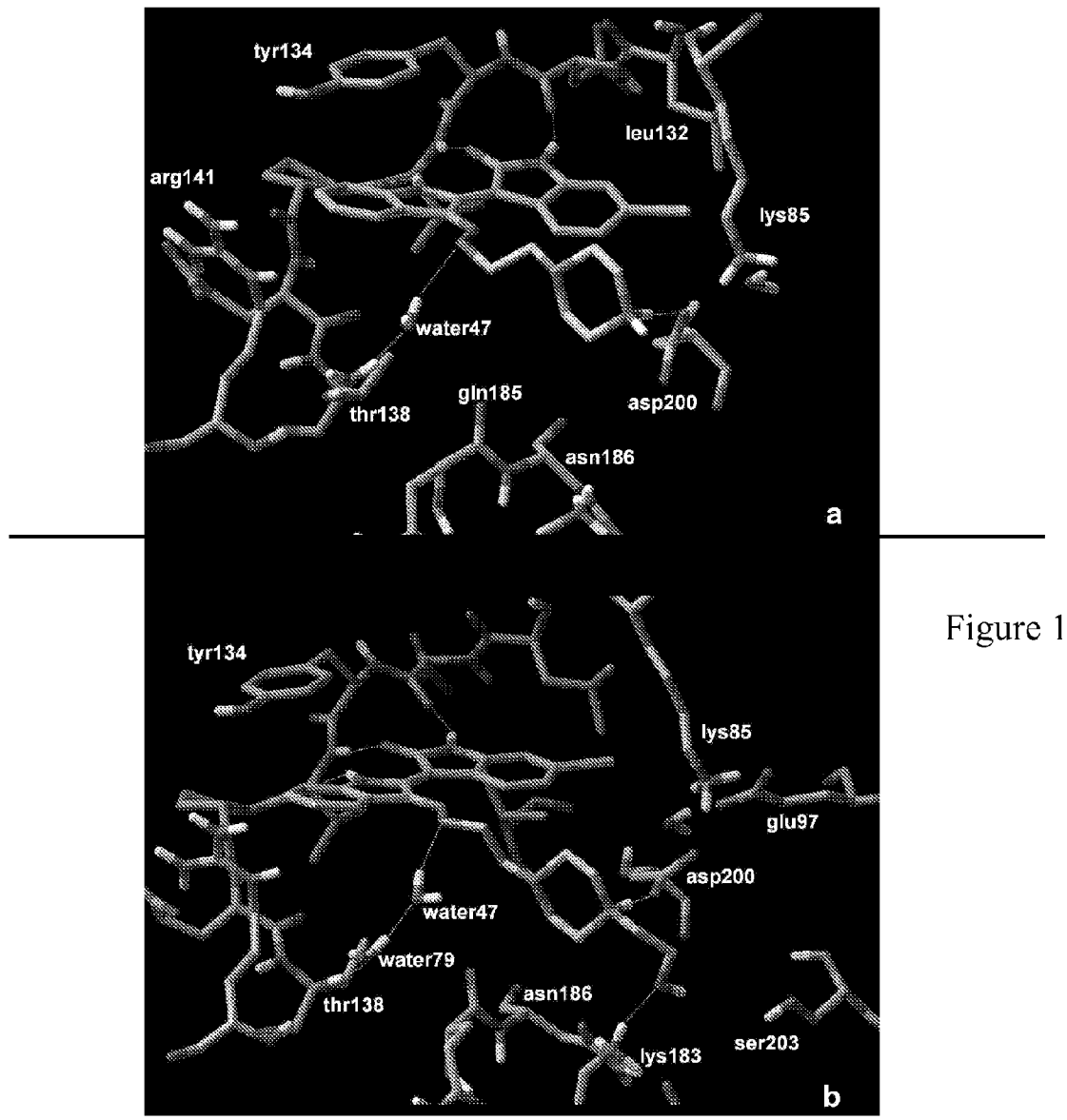
FIGS. 1a and 1b: the binding mode of analogues 11 (a) and 13 (b) to the binding pocket of GSK-3β. The piperazine substitution of both analogues interacts with asp200 and residues located at the phosphate sub-site of the binding pocket in addition to the hydrogen bonds (yellow dashed lines) formed between the indirubin scaffold and the receptor backbone

All chemicals were purchased from Aldrich Chemical Co. NMR spectra were recorded on Bruker DRX 400 and Biller AC 200 spectrometers [$^1$H (400 and 200 MHz) and $^{13}$C (50 MHz)]; chemical shifts are expressed in ppm downfield from TMS. The $^1$H—$^1$H and the $^1$H—$^{13}$C NMR experiments were performed using standard Bruker microprograms. Melting points were determined with a Sanyo Gallencamp apparatus. MS spectra were determined on a MSQ Thermofinnigan spectrometer. All UV/vis spectra were recorded on a Shimadzu UV-160A spectrophotometer.

Solubility Measurements. Equilibrium solubilities were determined by adding an excess amount of solid to the medium (water, double distilled) followed by 5 min of sonification and overnight equilibration by stirring at ambient temperature (25±0.1° C.). The samples were centrifuged and aliquots were removed. Standard solutions were prepared for each compound in order to quantify the aforementioned saturated solutions, and reference curves were plotted for each compound. The absorbance of each saturated and standard solution was measured with a UV/vis spectrophotometer at wavelength that varied between 515 and 518 nm.

The results are given in Table 1 which gives the water solubility of indirubin salts and calculated physicochemical properties pKa and logD at pH 7.4 of corresponding bases.

| No. | Solubility (g/l) | pKa | LogD |
| --- | --- | --- | --- |
| 6BIO | <0.005 | — | 2.59 |
| 16 | 0.141 | 8.59 | 1.69 |
| 17 | 0.192 | 9.38 | 1.19 |
| 18 | 0.195 | 9.18 | 1.16 |
| 21 | 1.45 | 7.48 | 1.79 |
| 22 | 1.61 | 8.85 | −0.87 |
| 23 | 1.50 | 7.65 | 1.74 |
| 24 | 1.14 | 7.65 | 1.41 |
| 25 | 0.57 | 7.47 | 1.90 |
| 26 | 4.253 | 7.58 | 1.46 |

General Procedure for the Preparation of the Ethers 1-3.

To a solution of 6-Bromoindirubin-3'-oxime (1.0 g, 2.83 mmol) in DMF (90 ml) were added triethylamine (0.5 ml) and the appropriate bromide (2 equiv.) under Ar, and the mixture was stirred for 17 h. at room temperature. Then water (300 ml) was added and the precipitate formed was collected by filtration and washed with water.

Data for (2'Z-3'E)-6-Bromoindirubin-3-[O-(2-bromoethyl)-oxime] (1).

Yield: 95%. Mp 252° C. $^1$H NMR (400 MHz, DMSO d-$_6$, δ ppm, J in Hz) 11.67 (1H, s, H-1'), 10.93 (1h, s, H-1), 8.49 (1H, d, J=8.3 Hz, H-4), 8.21 (1H, d, J=7.8 Hz, H-4'), 7.45 (2H, brs, H-6', H-7'), 7.16 (1H, dd, J=8.3/2.0 Hz, H-5), 7.07 (2H, m, H-5', H-7), 4.93 (2H, t, J=5.6 Hz, H-1"), 3.97 (2H, t, J=5.6 Hz, H-2"). APCI-MS m/z 462, 464, 466 (M+H)$^+$. Anal. ($C_{18}H_{13}N_3O_2Br_2$) C, H, N.

Data for (2'Z-3'E)-6-Bromoindirubin-3'-[O-(2-hydroxyethyl)-oxime] (2). Yield: 96%. Mp>300° C. $^1$H NMR (400 MHz, DMSO d-$_6$, δ ppm, J in Hz) 11.70 (1H, brs, H-1'), 10.90 (1H, brs, H-1), 8.54 (1H, d, J=8.4 Hz, H-4), 8.18 (1H, d, J=7.6 Hz, H-4'), 7.44 (2H, m, H-7', H-6'), 7.16 (1H, dd, J=8.4/1.9 Hz, H-5), 7.05 (2H, m, H-5', H-7), 5.02 (1H, t, J=5.4 Hz, —OH), 4.62 (2H, t, J=4.8 Hz, H-1"), 3.89 (2H, m, H-2"). CI-MS m/z 400, 402 (M+H)$^+$. Anal. ($C_{18}H_{14}N_3O_3Br$) C, H, N.

Data for (2'Z-3'E)-6-Bromoindirubin-3'-[O-(2,3-dihydroxypropyl)-oxime](3). Yield: 95%. Mp>300° C. $^1$H NMR (400 MHz, DMSO d-$_6$, δ ppm, J in Hz) 11.70 (1H, s, H-1'), 10.90 (1H, s, H-1), 8.56 (1H, d, J=8.5 Hz, H-4), 8.17 (1H, d, J=7.7 Hz, H-4'), 7.44 (2H, m, H-6', H-7'), 7.15 (1H, dd, J=8.5, 1.9 Hz, H-5), 7.06 (1H, m, H-5'), 7.03 (1H, d, J=1.9 Hz, H-7), 5.14 (1H, d, J=5.0 Hz, —CHOH), 4.84 (1H, t, J=5.6 Hz, —CH$_2$OH), 4.65 (1H, dd, J=10.9, 3.7 Hz, H-1"a), 4.50 (1H, dd, J=10.9, 6.6 Hz, H-1"b), 3.99 (1H, m, H-2"), 3.50 (2H, m, H-3"). APCI-MS (+) m/z 430, 432 (M+H)$^+$. Anal. ($C_{19}H_{16}N_3O_4Br_2$) C, H, N.

Data for (2'Z-3'E)-6-Bromoindirubin-3'-[O-(N,N-diethylcarbamyl)-oxime] (4).

To a solution of 6-Bromoindirubin-3'-oxime (36 mg, 0.11 mmol) in DMF (10 ml) were added triethylamine (0.5 ml) and 0.3 ml (3.66 mmol) N,N-diethylcarbamylchloride under Ar, and the mixture was stirred for 12 h. at room temperature. Then water (40 ml) was added and the precipitate formed was collected by filtration and washed with water to give 4 quantitatively. Yield: 90%. Mp 237° C. $^1$H-NMR (400 MHz, pyridine d-$_5$, δ ppm, J in Hz) 12.36 (1H, s, H-1'), 12.15 (1H, s, H-1), 9.93 (1H, d, J=8.6 Hz, H-4), 8.13 (1H, d, J=7.8 Hz, H-4'), 7.61 (1H, dd, J=8.6/1.9 Hz, H-5), 7.43 (1H, m, H-6'), 7.35 (1H, d, J=1.9 Hz, H-7'), 7.14-7.06 (2H, m, H-5', H-7), 3.44 (4H, brs, —N(CH$_2$CH$_3$)$_2$), 1.18 (6H, t, J=7.0 Hz, —N(CH$_2$CH$_3$)$_2$). APCI-MS (+) m/z 455, 457 (M+H)$^+$. Anal. ($C_{21}H_{19}N_4O_3Br$) C, H, N. fix above breaks Scheme 1

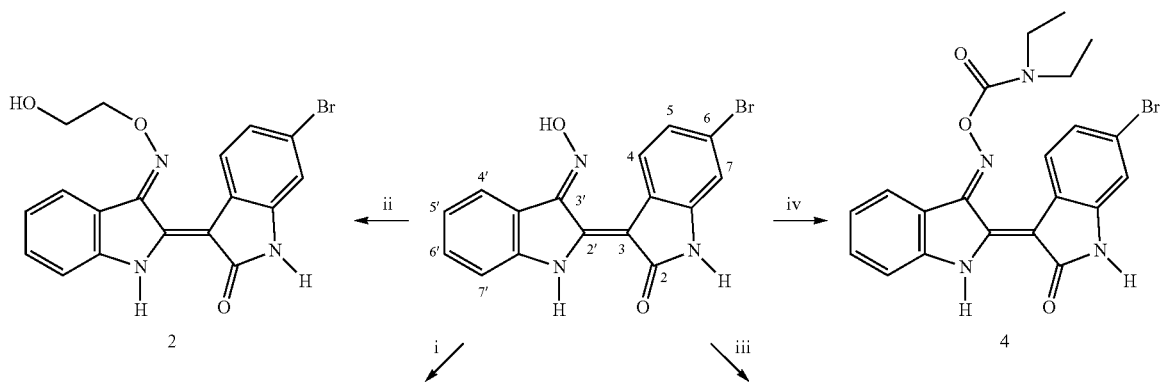

-continued

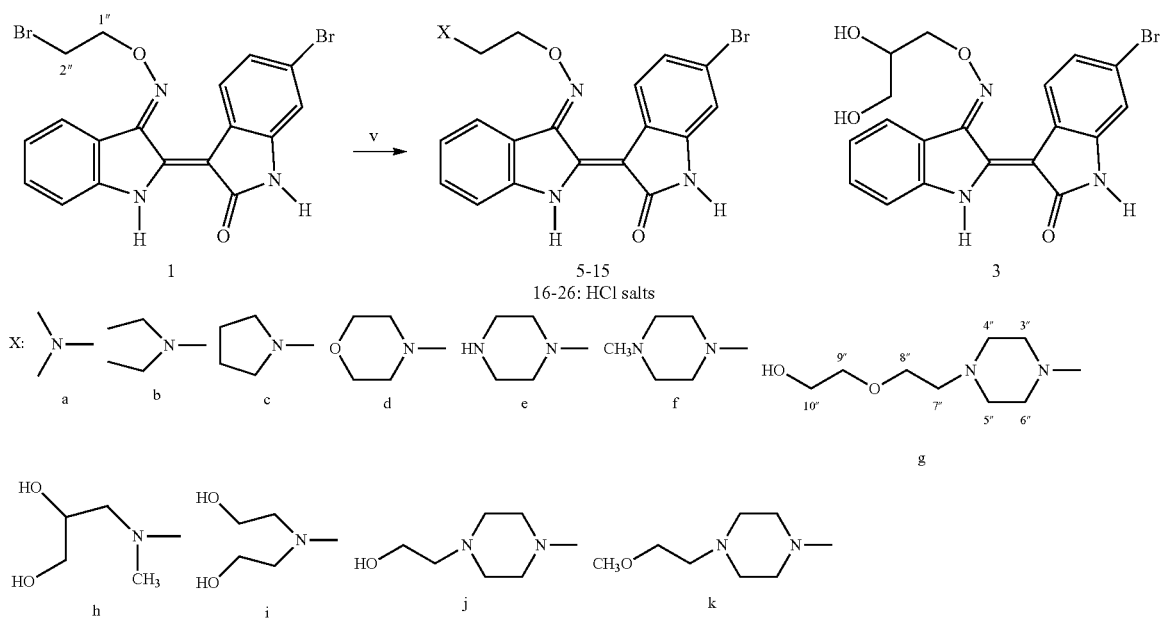

Reagents: (i) dibromoethane, triethylamine, DMF anh., 25° C.; (ii) 2-bromoethanol, triethylamine, DMF anh., 25° C.; (iii) 3-bromo-1,2-propanediol, triethylamine, DMF anh., 25° C. (iv) N,N-diethylcarbamyl chloride, triethylamine, DMF anh., 25° C. (v) DMF anh., 25° C., amine a-k General Procedure for the Preparation of the Amines 5-15.

100 mg of 6-bromoindirubin-3'-[O-(2"-bromoethyl)-oxime] (1) was dissolved in 5 ml of anhydrous DMF. An excess of the appropriate amine was added under magnetic stirring and the mixture was then heated at 50° C. After the completion of the reaction, the mixture was poured into water (30 ml) and the precipitate was filtered and washed with water and cyclohexane. Dimethylamine, diethylamine, pyrrolidine, morpholine, diethanolamine, 3-methylamine-1,2-propanediol, piperazine, 1-methylpiperazine, 1-(2-methoxyethyl) piperazine, 1-(2-hydroxyethyl) piperazine and 1-[2-(2-hydroxyethoxy)-ethyl]piperazine afforded products (5)-(15), correspondingly, in qualitative yields.

Data for (2'Z-3'E)-6-Bromoindirubin-3'-[O-(2-dimethylaminoethyl)-oxime] (5). Mp 230° C. $^1$H NMR (400 MHz, DMSO d-$_6$, δ ppm, J in Hz) 11.71 (1H, brs, H-1'), 10.92 (1H, brs, H-1), 8.55 (1H, d, J=8.5 Hz, H-4), 8.14 (1H, d, J=7.5 Hz, H-4'), 7.44 (2H, d, J=4.1 Hz, H-6', H-7'), 7.15 (1H, dd, J=8.5/2.0 Hz, H-5), 7.05 (2H, m, H-5', H-7) 4.69 (2H, t, J=5.8 Hz, H-1"), 2.80 (2H, t, J=5.8 Hz, H-2"), 2.27 (6H, s, —N(C$\underline{H}_3$)$_2$). APCI-MS m/z 427, 429 (M+H)$^+$. Anal. (C$_{20}$H$_{19}$N$_4$O$_2$Br) C, H, N.

Data for (2'Z-3'E)-6-Bromoindirubin-3'-[O-(2-diethylaminoethyl)-oxime] (6). Mp 232° C. $^1$H NMR (400 MHz, DMSO d-$_6$, δ ppm, J in Hz) 11.71 (1H, s, H-1'), 10.92 (1H, s, H-1), 8.55 (1H, d, J=8.2 Hz, H-4), 8.16 (1H, d, J=7.8 Hz, H-4'), 7.44 (2H, d, J=3.4 Hz, H-6', H-7'), 7.13 (1H, dd, J=8.2/2.1 Hz, H-5), 7.09-7.02 (2H, m, H-7, H-5'), 4.65 (2H, t, J=6.0 Hz, H-1"), 2.94 (2H, t, J=6.0 Hz, H-2"), 2.58 (2H, q, J=7.2 Hz, —N(C$\underline{H}_2$CH$_3$)$_2$), 0.98 (6H, t, J=7.2 Hz, —N(CH$_2$C$\underline{H}_3$)$_2$). APCI-MS (+) m/z 455, 457 (M+H)$^+$. Anal. (C$_{22}$H$_{23}$N$_4$O$_2$Br) C, H, N.

Data for (2'Z-3'E)-6-Bromoindirubin-3'-[O-(2-pyrrolidin-1-ylethyl)oxime] (7). Mp 208° C. $^1$H NMR (400 MHz, DMSO d-$_6$, δ ppm, J in Hz) 11.70 (1H, s, H-1'), 10.93 (1H, s, H-1), 8.54 (1H, d, J=8.5 Hz, H-4), 8.14 (1H, d, J=7.7 Hz, H-4'), 7.45 (2H, m, H-6', H-7'), 7.14 (1H, d, J=8.5/1.9 Hz, H-5), 7.05 (2H, m, H-5', H-7), 4.70 (2H, t, J=5.8 Hz, H-1"), 2.98 (2H, brt, J=5.8 Hz, H-2"), 2.57 (4H, brs, H-3", H-6"), 1.69 (4H, m, H-4", H-5"). APCI-MS (+) m/z 453, 455 (M+H)$^+$. Anal. (C$_{22}$H$_{21}$N$_4$O$_2$Br) C, H, N.

Data for (2'Z-3'E)-6-Bromoindirubin-3'-[O-(2-morpholin-1-ylethyl)oxime] (8). Mp 235° C. $^1$H NMR (400 MHz, DMSO d-$_6$, δ ppm, J in Hz) 11.70 (1H, s, H-1'), 10.90 (1H, s, H-1), 8.52 (1H, d, J=8.5 Hz, H-4), 8.15 (1H, d, J=7.6 Hz, H-4'), 7.43 (2H, m, H-6', H-7'), 7.14 (1H, dd, J=8.5/1.9 Hz, H-5), 7.05 (1H, m, H-5'), 7.02 (1H, d, J=1.9 Hz, H-7), 4.70 (2H, t, J=5.8 Hz, H-1"), 3.57 (4H, t, J=4.5 Hz, H-4", H-5"), 2.86 (2H, t, J=5.8 Hz, H-2"), 2.50 (4H, m, H-3", H-6", overlapped with DMSO). APCI-MS (+) m/z 469, 471 (M+H)$^+$. Anal. (C$_{22}$H$_{21}$N$_4$O$_3$Br) C, H, N.

Data for (2'Z-3'E)-6-Bromoindirubin-3'-[O-(2-(N,N-(2-hydroxyethyl)aminoethyl) oxime] (9). Mp 201° C. $^1$H NMR (400 MHz, pyridine d-$_5$, δ ppm, J in Hz) 12.31 (1H, brs, H-1'), 12.25 (1H, brs, H-1), 8.93 (1H, d, J=8.2 Hz, H-4), 8.42 (1H, d, J=7.8 Hz, H-4'), 7.47 (1H, dd, J=8.2, 1.8 Hz, H-5), 7.39 (1H, d, J=1.8 Hz, H-7), 7.34 (1H, t, J=7.2 Hz, H-6'), 7.04 (2H, m, H-5', H-7'), 5.89 (1H, brs, —OH), 4.86 (2H, t, J=6.3 Hz, H-1"), 4.00 (4H, m, —N(CH$_2$C$\underline{H}_2$OH)$_2$), 3.38 (2H, t, J=6.3 Hz, H-2"), 3.08 (4H, t, J=5.9 Hz, —N(C$\underline{H}_2$CH$_2$OH)$_2$). APCI-MS (+) m/z 487, 489 (M+H)$^+$. Anal. (C$_{22}$H$_{23}$N$_4$O$_4$Br) C, H, N.

Data for (2'Z-3'E)-6-Bromoindirubin-3'-(O-{2-[-methyl, N-(2,3-dihydroxypropyl) amino]ethyl}oxime] (10). Mp 195° C. $^1$H NMR (400 MHz, pyridine d-$_5$, δ ppm, J in Hz) 12.27 (2H, m, H-1, H-1'), 8.90 (1H, d, J=8.8 Hz, H-4), 8.41 (1H, d, J=7.5 Hz, H-4'), 7.46 (1H, dd, J=8.8,1.8 Hz, H-5), 7.38 (1H, d, J=1.8 Hz, H-7'), 7.36 (1H, t, J=7.5 Hz, H-6'), 7.05 (2H, m, H-5', H-7), 4.80 (2H, t, J=6.1 Hz, H-1"), 4.29 (1H, m, H-4"), 4.11 (1H, dd, J =11.0, 4.6 Hz, H-5"a), 4.04 (1H, dd, J=11.0, 5.5 Hz, H-5"b), 3.14 (2H, t, J=6.1 Hz, H-2"), 2.93 (2H, m, H-3"), 2.49 (3H, s, —NC$\underline{H}_3$). CI-MS m/z 487, 489 (M+H)$^+$. Anal. (C$_{22}$H$_{23}$N$_4$O$_4$Br) C, H, N.

Data for (2'Z-3'E)-6-Bromoindirubin-3'-[O-(2-piperazine-1-ylethyl)oxime] (11). Mp 255° C. (dec.). $^1$H NMR (400 MHz, DMSO d-$_6$, δ ppm, J in Hz) 11.69 (1H, s, H-1'), 10.92

(1H, s, H-1), 8.53 (1H, d, J=8.5 Hz, H-4), 8.15 (1H, d, J=7.4 Hz, H-4'), 7.43 (2H, m, H-6', H-7'), 7.14 (1H, d, J=8.5 Hz, H-5), 7.03 (2H, m, H-5', H-7), 4.69 (2H, br t, H-1''), 2.83 (2H, br t, H-2''), 2.71 (4H, brs, H-4'', H-5''), 2.46 (4H, brs, H-3'', H-6'', partially overlapped with DMSO). APCI-MS (+) m/z 468, 470 (M+H)$^+$. Anal. ($C_{22}H_{22}N_5O_2Br$) C, H, N.

Data for (2'Z-3'E)-6-Bromoindirubin-3'-{O-[2-(4-methyl-piperazin-1-yl)ethyl]oxime}(12). Mp 222° C. $^1$H NMR (400 MHz, DMSO d-$_6$, δ ppm, J in Hz) 11.68 (1H, s, H-1'), 10.90 (1H, s, H-1), 8.40 (1H, d, J=8.5 Hz, H-4), 8.14 (1H, d, J=7.7 Hz, H-4') 7.42 (2H, m, H-6', H-7'), 7.13 (1H, dd, J=8.5/1.9 Hz, H-5), 7.04 (1H, m, H-5'), 7.02 (1H, d, J=1.9 Hz, H-7), 4.68 (2H, t, J=5.9 Hz, H-1''), 2.85 (2H, t, J=5.9 Hz, H-2''), 2.50 (4H, brs, H-3'', H-6'', overlapped with DMSO), 2.31 (4H, brs, H-4'', H-5''), 2.13 (3H, s, —NC$\underline{H}_3$). APCI-MS (+) m/z 482, 484 (M+H)$^+$. Anal. ($C_{23}H_{24}N_5O_2Br$) C, H, N.

Data for (2'Z-3'E)-6-Bromoindirubin-3'-O-{2-[4-(2-hydroxyethyl)piperazin-1-yl]ethyl}oxime) (13). Mp 187° C. $^1$H NMR (400 MHz, DMSO d-$_6$, δ ppm, J in Hz) 8.52 (1H, d, J=8.5 Hz, H-4), 8.16 (1H, d, J=7.6 Hz, H-4'), 7.43 (2H, m, H-6', H-7'), 7.13 (1H, dd, J =8.5/1.8 Hz, H-5), 7.05 (1H, m, H-5'), 7.02 (1H, d, J=1.8 Hz, H-7), 4.69 (2H, t, J=5.7 Hz, H-1''), 3.45 (2H, t, J=6.3 Hz, H-8''), 2.85 (2H, t, J=5.7 Hz, H-2''), 2.50 (4H, H-3'', H-6'', overlapped with DMSO), 2.42 (4H, H-4'', H-5''), 2.34 (2H, t, J=6.3 Hz, H-7''). APCI-MS (+) m/z 512, 514 (M+H)$^+$. Anal. ($C_{24}H_{26}N_5O_3Br$) C, H, N.

Data for (2'Z-3'E)-6-Bromoindirubin-3'-O-{2-[4-(2-methoxyethyl)piperazin-1-yl]ethyl}oxime) (14). Mp 184° C. $^1$H NMR (400 MHz, DMSO d-$_6$, δ ppm, J in Hz) 11.70 (1H, s, H-1'), 10.90 (1H, s, H-1), 8.50 (1H, d, J=8.5 Hz, H-4), 8.16 (1H, d, J=7.6 Hz, H-4'), 7.44 (2H, m, H-6', H-7'), 7.15 (1H, dd, J=8.5, 1.7 Hz, H-5), 7.07 (2H, m, H-5', H-7), 4.70 (2H, t, J=5.6 Hz, H-1''), 3.40 (2H, H-8'', overlapped with water), 3.21 (3H, s, —OC$\underline{H}_3$), 2.87 (2H, brt, H-2''), 2.66-2.40 (H-4'', H-5'', H-3'', H-6'', $\underline{H}$ 7''), overlapped with DMSO). APCI-MS (+) m/z 526, 528 (M+H)$^+$. Anal. ($C_{25}H_{28}N_5O_3Br$) C, H, N.

Data for (2'Z-3'E)-6-Bromoindirubin-3'-[O-(2-{4-[2-(2-hydroxyethoxy)-ethyl]piperazin-1-yl}ethyl)oxime] (15). Mp 183° C. $^1$H NMR (400 MHz, pyridine d-$_5$, δ ppm, J in Hz) 12.31 (1H, s, H-1'), 12.25 (1H, s, H-1), 8.89 (1H, d, J=8.3 Hz, H-4), 8.39 (1, d, J=7.9 Hz, H-4'), 7.45-7.33 (3H, m, H-5, H-7', H-6'), 7.09 (2H, m, H-5', H-7) 4.78 (2H, t, J=5.8 Hz, H-1''), 3.96 (2H, t, J=5.0 Hz, H-10''), 3.70 (2H, t, J=5.0 Hz, H-9''), 3.66 (2H, t, J=5.8 Hz, H-8''), 2.94 (2H, t, J=5.8 Hz, H-2''), 2.68 (2H, brs, H-3'', H-6''), 2.57 (8H, t, J=5.8 Hz, H-4'', H-5'', H-7''). APCI-MS (+) m/z 556, 558 (M+H)$^+$. Anal. ($C_{26}H_{30}N_5O_4Br$) C, H, N.

General Procedure for the Preparation of the Amine Salts 16-26. The appropriate indirubin derivative 5-15 (0.10 mmol) was dissolved in anhydrous THF (50 ml) and 0.2 ml of a saturated solution of hydrochloric acid in ether was added dropwise. The reaction mixture was left to cool in an ice bath and the precipitate formed was collected by filtration.

Data for (2'Z-3')-6-Bromoindirubin-3'-[O-(2-dimethylaminoethyl)oxime]Hydrochloride (16). $S_w$ (g/l) 0.141. $^1$H-NMR (400 MHz, DMSO d-$_6$, δ ppm J in Hz) 11.70 (1H, s, H-1'), 10.97 (1H, s, H-1), 8.49 (1H, d, J=8.3 Hz, H-4), 8.22 (1H, J=7.4 Hz, H-4'), 7.46 (2H, m, H-7, H-6'), 7.20 (1H, dd, J=8.3/1.7 Hz, H-5), 7.05 (2H, m, H-5', H-7'), 4.95 (2H, brs, H-1''), 3.58 (2H, m, H-2''), 2.81 (6H, brs, —N(CH$_3$)$_2$). Anal. ($C_{20}H_{20}N_4O_2BrCl$) C, H, N.

Data for (2'Z-3')-6-Bromoindirubin-3'-[O-(2-diethylaminoethyl)oxime]Hydrochloride (17). $S_w$ (g/l) 0.192. $^1$H NMR (400 MHz, DMSO d-$_6$, δ ppm, J in Hz) 11.70 (1H, s, H-1'), 10.98 (1H, s, H-1), 8.49 (1H, d, J=8.6 Hz, H-4), 8.21 (1H, d, J=7.4 Hz, H-4'), 7.47 (2H, m, H-6', H-7), 7.21 (1H, dd, J=8.6/1.9 Hz, H-5), 7.09-7.04 (2H, m, H-5', H-7'), 5.00 (2H, brs, H-1''), 3.58 (2H, brs, H-2''), 3.24 (4H, brs, —N(C$\underline{H}_2$CH$_3$)$_2$), 1.21 (6H, t, J=7.0 Hz, —N(CH$_2$C$\underline{H}_3$)$_2$). Anal. ($C_{22}H_{24}N_4O_2BrCl$) C, H, N.

Data for (2'Z-3')-6-Bromoindirubin-3'-[O-(2-pyrrolidin-1-ylethyl)oxime]Hydrochloride (18). $S_w$ (g/l) 0.195. $^1$H NMR (400 MHz, DMSO d-$_6$, δ ppm, J in Hz) 11.71 (1H, s, H-1'), 10.97 (1H, s, H-1), 8.48 (1H, d, J=8.6 Hz, H-4), 8.22 (1H, d, J=7.4 Hz, H-4'), 7.44-7.52 (2H, m, H-7, H-6'), 7.20 (1H, dd, J=8.6/1.9 Hz, H-5), 7.07 (2H, m, H-5', H-7'), 4.94 (2H, brs, H-1''), 3.64 (2H, brs, H-2''), 3.13 (4H, m, H-3'', H-6''), 2.02 (4H, m, H-4'', H-5''). Anal. ($C_{22}H_{22}N_4O_2BrCl$) C, H, N.

Data for (2'Z-3')-6-Bromoindirubin-3'-[O-(2-morpholin-1-ylethyl)oxime]Hydrochloride (19). $^1$H NMR (400 MHz, DMSO d-$_6$, δ ppm, J in Hz) 11.69 (1H, s, H-1'), 10.98 (1H, s, H-1), 8.47 (1H, d, J=8.5 Hz, H-4), 8.22 (1H, d, J=7.8 Hz, H-4') 7.45 (2H, m, H-7, H-6'), 7.21 (1H, dd, J=8.3, 1.8 Hz, H-5), 7.06 (2H, m, H-5', H-7') 5.05 (2H, brs, H-1''), 3.95 (2H, m, H-2''), 3.75 (4H, m, H-4'', H-5''), 3.27 (4H, H-3'', H-6'', overlapped with water). Anal. ($C_{22}H_{22}N_4O_3BrCl$) C, H, N.

Data for (2'Z-3')-6-Bromoindirubin-3'-[O-(2-(N,N-(2-hydroxyethyl)aminoethyl)oxime] (20). $^1$H NMR (400 MHz, DMSO d-$_6$, δ ppm, J in Hz) 11.71 (1H, s, H-1'), 10.98 (1H, s, H-1), 8.48 (1H, d, J=8.3 Hz, H-4), 8.22 (1H, d, J=7.9 Hz, H-4'), 7.46 (2H, m, H-7, H-6'), 7.21 (1H, dd, J=8.3/1.8 Hz, H-5), 7.06 (2H, m, H-5', H-7'), 5.35 (2H, brs, OH), 5.03 (2H, brs, H-1'), 3.84 (2H, brs, H-2'), 3.78 (4H, brs, —N(CH$_2$C$\underline{H}_2$OH)$_2$), 3.38 (4H, m, —N(C$\underline{H}_2$CH$_2$OH)$_2$, overlapped with water). Anal. ($C_{22}H_{24}N_4O_4BrCl$) C, H, N.

Data for (2'Z-3')-6-Bromoindirubin-3'-O-{2-[N-methyl, N-(2,3-dihydroxypropyl)amino]ethyl}oxime]Hydrochloride (21). $S_w$ (g/l) 1.45. $^1$H NMR (400 MHz, DMSO d-$_6$, δ ppm, J in Hz) 11.69 (1H, s, H-1'), 10.96 (1H, s, H-1), 8.48 (1H, d, J=8.5 Hz, H-4), 8.20 (1H, d, J=7.9 Hz, H-4'), 7.4 (2H, m, H-7, H-6'), 7.19 (1H, dd, J=8.5/ 1.8 Hz, H-5), 7.05 (2H, m, H-5', H-7'), 4.95 (2H, brs, H-1''), 3.89 (1H, brs, H-4''), 3.38 (4H, H-3', H-5', overlapped with water), 2.83 (2H, brs, H-3'), 2.50 (3H, —N(C$\underline{H}_3$), overlapped with DMSO).Anal. ($C_{22}H_{24}N_4O_4BrCl$) C, H, N.

Data for (2'Z-3'E)-6-Bromoindirubin-3'-[O-(2-piperazine-1-ylethyl)oxime]Dihydrochloride (22). $S_w$ (g/l) 1.61. $^1$H NMR (400 MHz, D$_2$O, δ ppm, J in Hz) 7.65 (1H, d, J=8.5 Hz, H-4), 7.55 (1H, d, J=7.5 Hz, H-4'), 7.26 (1H, t, J=7.5 Hz, H-6'), 6.85 (1H, t, J=7.2 Hz, H-5'), 6.76 (1H, d, J=8.5 Hz, H-5), 6.72 (1H, d, J=7.5 Hz, H-7'), 6.54 (1H, s, H-7), 4.42 (2H, brt, H-1''), 3.38 (4H, brt, H-4'', H-5''), 3.11 (6H, brs, H-3'', H-6'', H-2''). Anal. ($C_{22}H_{24}N_5O_2BrCl_2$) C, H, N.

Data for (2'Z-3'E)-6-Bromoindirubin-3'-{O-[2-(4-methylpiperazin-1-yl)ethyl]oxime}Dihydrochloride (23). $S_w$ (g/l) 1.50. $^1$H NMR (400 MHz, D$_2$O, δ ppm, J in Hz) 7.63 (1H, d, J=8.2 Hz, H-4), 7.53 (1H, d, J=7.5, H-4'), 7.25 (1H, t, J=7.6 Hz, H-6'), 6.84 (1H, t, J=7.6 Hz, H-5'), 6.75 (1H, d, J=8.2 Hz, H-5), 6.70 (1H, d, J=7.5 Hz, H-7'), 6.53 (1H, s, H-7), 4.39 (2H, brs, H-1''), 3.39 (4H, brs, H-3'', H-6''), 3.11 (6H, brs, H-2'', H4'', H-5''), 2.90 (3H, s, —NC$\underline{H}_3$). Anal. ($C_{23}H_{26}N_5O_2BrCl_2$) C, H, N.

Data for (2'Z-3')-6-Bromoindirubin-3'-O-{2-[4-(2-hydroxyethyl)piperazin-1-yl]ethyl}oxime)Dihydrochloride (24). $S_w$ (g/l) 1.14. $^1$H NMR (400 MHz, D$_2$O, δ ppm, J in Hz) 7.68 (1H, d, J=8.5 Hz, H-4), 7.56 (1H, d, J=7.4 Hz, H-4'), 7.27 (1H, brt, J=7.2 Hz, H-6'), 6.85 (1H, brt, J=7.2 Hz, H-5'), 6.78 (1H, d, J=8.5 Hz, H-5), 6.73 (1H, d, J=7.4 Hz, H-7'), 6.57 (1H, s, H-7), 4.42 (2H, brs, H-1''), 3.89 (2H, brs, H-8''), 3.39 (4H, brs, H-3'', H-6''), 3.26 (2H, brs, H-7''), 3.12 (6H, brs, H-2'', H-4'', H-5''). Anal. ($C_{24}H_{28}N_5O_3BrCl_2$) C, H, N.

Data for (2'Z-3'E)-6-Bromoindirubin-3'-O-{2-[4-(2-methoxyethyl)piperazin-1-yl]ethyl}oxime)Dihydrochloride (25). $S_w$ (g/l) 0.57. $^1$H NMR (400 MHz, D$_2$O, δ ppm, J in Hz) 7.70

(1H, brs, H-4), 7.61 (1H, brs, H-4'), 7.28 (1H, brt, J=7.2 Hz, H-6'), 6.88 (1H, brt, J=7.5 Hz, H-5'), 6.77 (2H, brs, H-5, H-7'), 6.58 (1H, s, H-7), 4.52 (2H, brs, H-1''), 3.74 (2H, brs, H-8''), 3.55-3.22 (12H, H-2'', H-3'', H-4'', H-5'', H-6'', H-7''), 3.35 (3H, s, —OC$\underline{H}_3$). Anal. ($C_{25}H_{30}N_5O_3BrCl_2$) C, H, N.

Data for (2'Z-3'E)-6-Bromoindirubin-3'-[O-(2-{4-[2-(2-hydroxyethoxy)-ethyl]piperazin-1-yl}ethyl)oxime]Dihydrochloride (26). $S_w$ (g/l) 4.253. $^1$H NMR (400 MHz, $D_2O$, δ ppm, J=in Hz) 7.54 (1H, d, J=8.1 Hz, H-4), 7.44 (1H, d, J=7.2 Hz, H-4'), 7.21 (1H, brt, J=7.6 Hz, H-6'), 6.78 (1H, brt, J=7.2 Hz, H-5'), 6.69 (1H, d, J=7.2 Hz, H-7'), 6.61 (1H, d, J=8.1 Hz, H-5), 6.34 (1H, s, H-7), 4.28 (2H, brs, H-1''), 3.82, 3.72, 3.63, (6H, H-8'', H-9'', H-10''), 3.46-2.72 (12H, H-2'', H-3'', H-4'', H-5'', H-6'', H-7'') Anal. ($C_{26}H_{32}N_5O_4BrCl_2$) C, H, N.

Biology

Kinase Preparation and Assays

Kinase activities were assayed in buffer A (10 mM $MgCl_2$, 1 mM EGTA, 1 mM DTT, 25 mM Tris-HCl pH 7.5, 50 µg heparin/ml) or C (homogenization buffer but 5 mM EGTA, no NaF and no protease inhibitors), at 30° C., at a final ATP concentration of 15 µM. Blank values were subtracted and activities calculated as pmoles of phosphate incorporated during a 30 mM incubation. The activities were expressed in % of the maximal activity, i.e. in the absence of inhibitors. Controls were performed with appropriate dilutions of dimethylsulfoxide. Phosphorylation of the substrate was assessed by the P81 phosphocellulose assay.

CDK1/cyclin B was extracted in homogenization buffer (60 mM β-glycerophosphate, 15 mM p-nitrophenylphosphate, 25 mM Mops (pH 7.2), 15 mM EGTA, 15 mM $MgCl_2$, 1 mM DTT, 1 mM sodium vanadate, 1 mM NaF, 1 mM phenylphosphate, 10 µg leupeptin/ml, 10 µg aprotinin/ml, 10 µg soybean trypsin inhibitor/ml and 100 µM benzamidine) from M phase starfish (*Marthasterias glacialis*) oocytes and purified by affinity chromatography on p9$^{CKShs1}$-sepharose beads, from which it was eluted by free p9$^{CKShs1}$ as previously described[4]. The kinase activity was assayed in buffer C, with 1 mg histone H1/ml, in the presence of 15 µM [γ-$^{33}$P] ATP (3,000 Ci/mmol; 10 mCi/ml) in a final volume of 30 µl. After 30 min. incubation at 30° C., 25 µl aliquots of supernatant were spotted onto 2.5×3 cm pieces of Whatman P81 phosphocellulose paper, and, 20 sec. later, the filters were washed five times (for at least 5 min. each time) in a solution of 10 ml phosphoric acid/liter of water. The wet filters were counted in the presence of 1 ml ACS (Amersham) scintillation fluid.

CDK5/p25 was reconstituted by mixing equal amounts of recombinant human CDK5 and p25 expressed in *E. coli* as GST (Glutathione-S-transferase) fusion proteins and purified by affinity chromatography on glutathione-agarose (p25 is a truncated version of p35, the 35 kDa CDK5 activator). Its activity was assayed with histone H1 in buffer C as described for CDK1/cyclin B.

GSK-3α/β was purified from porcine brain by affinity chromatography on immobilized axin[5]. It was assayed, following a 1/100 dilution in 1 mg BSA/ml 10 mM DTT, with 4 µM GS-1 (YRRAAVPPSPSLSRHSSPHQSpEDEEE), a GSK-3 specific substrate obtained from Millegen (Labege, France), in buffer A, in the presence of 15 µM [γ-$^{33}$P] ATP (3,000 Ci/mmol; 10 mCi/ml) in a final volume of 30 µl. After 30 min. incubation at 30° C., 25 µl aliquots of supernatant were processed as described above.

Cellular Assays

Cell Culture Conditions and Cell Survival Assessment

SH-SY5Y human neuroblastoma cell line was grown at 37° C. with 5% $CO_2$ in DMEM supplemented with 2 mM L-glutamine (Invitrogen, Cergy Pontoise, France), plus antibiotics (penicillin-streptomycin) from Lonza, and a 10% volume of fetal calf serum (FCS) (Invitrogen). Drug treatments were performed on exponentially growing cultures at the indicated time and concentrations. Control experiments were carried also using appropriate dilutions of DMSO. Cell viability was determined by means of the MTS (3-(4,5-dimethylthiazol-2-yl)-5-(3-carboxymethoxyphenyl)-2-(4-sulfophenyl)-2H-tetrazolium) method after 48 hr of treatment as previously described[6].

β-catenin Phosphorylation in SH-SY5Y Human Neuroblastoma Cells

Nearly confluent SH-SY5Y human neuroblastoma cells were grown in 96 plates in DMEM (supplemented with 10% FCS and antibiotics). Cells were co-treated with tested compounds and 2 µM MG132 (to allow accumulation of phosphorylated β-catenin) for 6 hours. Final DMSO concentration did not exceed 1%. Cells were then subjected to an ELISA assay using antibodies directed against Ser33/Ser37/Thr41-phosphorylated (1:1000) p-catenin obtained from Cell Signaling Technology. Results are expressed in percentage of maximal β-Catenin phosphorylation, i.e. in untreated cells exposed to MG132 only as positive control (100% phosphorylation).

Cell Culture and Luminescence Assay of Circadian Rhythmicity

These experiments used Rat-1 fibroblasts that have been stably transfected with a $P_{Per2}$::Fluc reporter construct that shows a robust circadian rhythm of luminescence as a gauge of clock-controlled Per2 promoter ($P_{Per2}$) activity[7]. The cells were cultured in DMEM (11965-092, GIBCO/Invitrogen) supplemented with 5% FBS, 50 units/ml penicillin, and 50 µg/ml streptomycin in a 5% $CO_2$ incubator at 37° C. Approximately 5×10$^5$ cells were seeded in a 35 mm dish at least 5 days before the experiment. Three days after the cells reached 100% confluence, the cells were treated with 0.1 µM dexamethasone (Sigma) for 1 h to synchronize the oscillators among the cells in the population. At the end of the treatment, the medium was replaced with assay medium [DMEM without phenol red, supplemented with bicarbonate (350 mg/L), 5% FBS, 10 mM HEPES (pH 7.2), antibiotics (25 units/ml penicillin, 25 µg/ml streptomycin), and 0.1 mM luciferin (Promega)]. Culture dishes were sealed with a 40-mm microscope glass cover slip and high-vacuum grease to prevent the evaporation of culture medium. The luminescence rhythm was monitored in a LumiCycle (Actimetrics Inc., Evanston, Ill., USA). Before being sealed, drugs were added to the culture dishes to different final concentrations and left continuously with the cells thereafter while the luminescence patterns were recorded for 5 days or more. DMSO was used as a solvent control. Regression analyses to determine period and phase of the luminescence rhythms were performed with the Chrono II program.

Electrophoresis and Western Blotting

Cells were resuspended, lysed for 30 min at 4° C. in Homogenization Buffer and sonicated. After centrifugation (14000 r.p.m. for 15 min at 4° C.), the protein concentration was determined in the supernatants by the Bradford protein assay (Bio-Rad). Following heat denaturation for 5 min, proteins were separated by 10% NuPAGE pre-cast Bis-Tris Acetate polyacrylamide mini gel (Invitrogen) with MOPS SDS running buffer. Proteins were transferred to 0.45 µm nitrocellulose filters (Schleicher and Schuell). These were blocked with 5% low fat milk in Tris-Buffered Saline—Tween-20, incubated overnight at 4° C. with antibodies directed against Ser33/Ser37/Thr41-phosphorylated β-catenin (1:1000) (Cell Signaling Technology) and analyzed by Enhanced Chemiluminescence (ECL, Amersham).

Results
Cytotoxicity of the 6BIO Derivatives

The effects of indirubins 1-26 on three protein kinases and on the survival of human neuroblastoma SH-SY5Y cells are given in Table 2. Indirubins were tested at various concentrations on GSK-3α/β, CDK1/cyclin B, CDK5/p25, as described in Experimental Section. $IC_{50}$ values, calculated from the dose-response curves, are reported in μM. The compounds were tested at various concentrations for their effects on SH-SY5Y cells survival after 48 h incubation as estimated using the MTS reduction assay. $IC_{50}$ values, calculated from the dose-response curves, are reported in μM.

| Cpd # | R | GSK3 | CDK1 | CDK5 | SH-SY5Y |
|---|---|---|---|---|---|
| 6BIO | H | 0.005 | 0.320 | 0.083 | 9.0 |
| 1 | —CH₂CH₂Br | 0.14 | >10 | >10 | >100 |
| 2 | —CH₂CH₂OH | 1.70 | 1.7 | 5.0 | >100 |
| 3 | —CH₂CH(OH)CH₂OH | 0.034 | 0.110 | 0.025 | 0.94 |
| 4 | N,N-diethylacetamide group | 0.03 | >10 | 10 | >100 |
| 5 | NCH₂CH₂ (diethylamino) | 0.033 | 0.490 | 0.100 | 5.4 |
| 16 | NCH₂CH₂ •HCl (diethylamino) | 0.029 | 0.19 | 0.053 | 5.8 |
| 6 | NCH₂CH₂ (diisopropylamino) | 0.035 | 0.09 | 0.02 | 78.0 |
| 17 | NCH₂CH₂ •HCl (diisopropylamino) | 0.027 | 0.19 | 0.04 | >100 |
| 9 | (HOCH₂CH₂)₂NCH₂CH₂ | 0.040 | 0.60 | 0.21 | 6.6 |
| 20 | (HOCH₂CH₂)₂NCH₂CH₂ •HCl | 0.041 | 1.00 | 0.10 | 9.0 |
| 10 | HOCH₂CH(OH)CH₂-N(CH₃)-CH₂CH₂ | 0.067 | 0.24 | 0.24 | 5.8 |

-continued
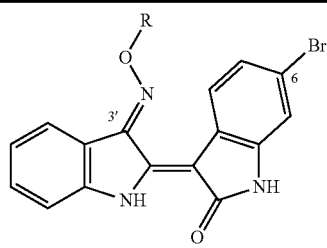
| Cpd # | R | GSK3 | CDK1 | CDK5 | SH-SY5Y |
|---|---|---|---|---|---|
| 21 | HO-CH(OH)-CH(OH)-CH2-N(CH3)-CH2CH2– •HCl | 0.023 | 0.15 | 0.10 | 6.0 |
| 7 | pyrrolidine-NCH2CH2– | 0.026 | 0.50 | 0.13 | 5.5 |
| 18 | pyrrolidine-NCH2CH2– •HCl | 0.054 | 0.45 | 0.10 | 4.2 |
| 8 | morpholine-NCH2CH2– | 0.060 | 1.10 | 0.60 | 72 |
| 19 | morpholine-NCH2CH2– •HCl | 0.110 | 1.80 | 0.90 | 74 |
| 11 | HN-piperazine-NCH2CH2– | 0.0033 | 0.3 | 0.2 | 13.2 |
| 22 | HN-piperazine-NCH2CH2– •2HCl | 0.0013 | 0.2 | 0.18 | 5.9 |
| 12 | CH3-N-piperazine-NCH2CH2– | 0.0070 | 0.4 | 0.4 | 5.4 |
| 23 | CH3-N-piperazine-NCH2CH2– •2HCl | 0.0050 | 0.3 | 0.3 | 5.4 |
| 13 | HO-CH2CH2-N-piperazine-NCH2CH2– | 0.0050 | 0.6 | 0.2 | 28.0 |
| 24 | HO-CH2CH2-N-piperazine-NCH2CH2– •2HCl | 0.0042 | 0.4 | 0.2 | 16.7 |
| 14 | CH3O-CH2CH2-N-piperazine-NCH2CH2– | 0.0110 | 2.8 | 0.5 | >100 |
| 25 | CH3O-CH2CH2-N-piperazine-NCH2CH2– •2HCl | 0.0200 | 1.0 | 0.4 | >100 |

-continued

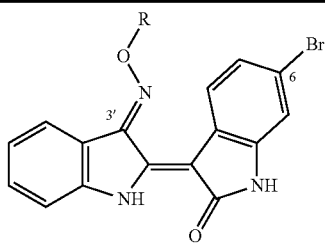

| Cpd # | R | GSK3 | CDK1 | CDK5 | SH-SY5Y |
|---|---|---|---|---|---|
| 15 | HO~~~O~~~N(piperazine)NCH₂CH₂ | 0.014 | 0.90 | 0.31 | 94.4 |
| 26 | HO~~~O~~~N(piperazine)NCH₂CH₂ •2HCl | 0.033 | 0.50 | 0.33 | 97.6 |

The indirubin derivatives of the invention were tested for their effects on survival of SH-SY5Y neuroblastoma cells using an MTS reduction assay. These assays revealed that increased potency on GSK-3 was not associated with enhanced cell death (Table 1). Analogues 13, 14 and 15 (and their corresponding salts, 24, 25, 26) had little cell death inducing activities. The $IC_{50}$ values were respectively 28 µM, >100 µM, 94 µM (salts: 17 µM, >100 µM, 98 µM) to compare with the $IC_{50}$ of 6BIO, 9 µM). Therefore the substituted piperazine ring extension, not only favours selectivity and efficacy towards GSK-3, allows better solubility, but also reduces their cytotoxicity. These features are particularly favorable for the use of these compounds in the study of GSK-3 in cellular systems, and also as potential therapeutic leads in the context of neurodegenerative diseases and diabetes.

Confirmation of Intracellular Inhibition of GSK-3 by Indirubins

Figure 2A:
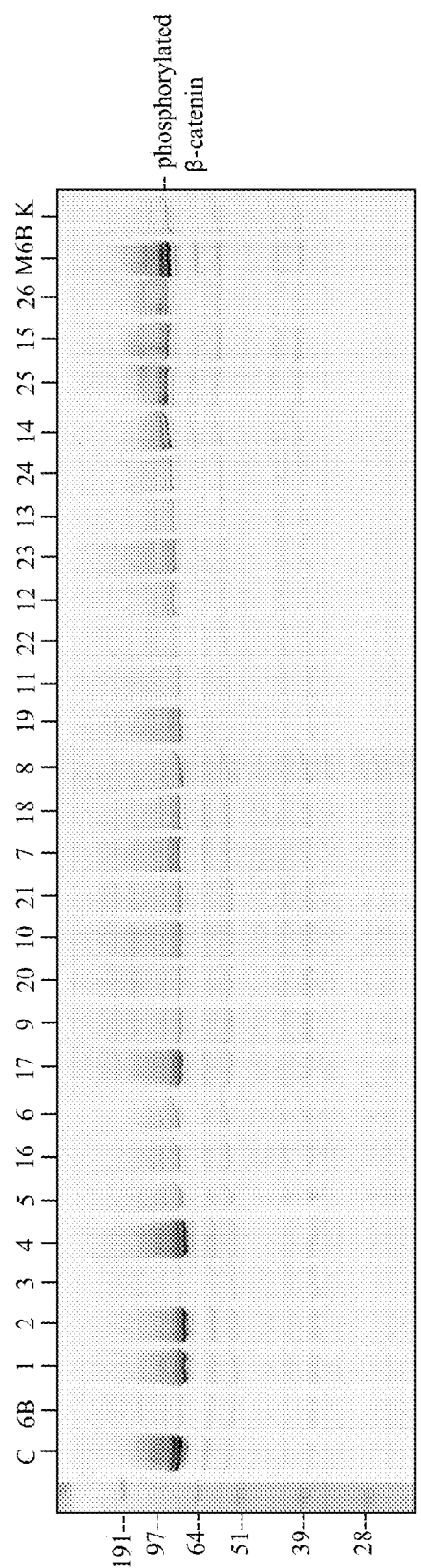
FIGS. 2a and 2b: the inhibition of β-catenin phosphorylation at GSK-3 phosphorylation sites by the indirubin derivatives. 2a. SH-SY5Y neuroblastoma cells were exposed for 6 hours to 10 μM of each indirubin, in the presence of a constant 2 μM level of the proteasome inhibitor MG132. The level of GSK-3-phosphorylated β-catenin was estimated by Western blotting following SDS-PAGE, using an antibody that specifically cross-reacts with GSK-3 phosphorylated β-catenin. Lack or reduction of the signal indicates that the indirubin has been able to inhibit GSK-3 within the neuroblastoma cells. C, control (DMSO); 6B, 6BIO; M6B, Methyl-6BIO (a control inactive analog of 6BIO); K, kenpaullone, a structurally unrelated GSK-3 inhibitor. 2b. Dose-response curves for a selection of indirubins were run in an ELISA assay using the same antibodies directed against GSK-3 phosphorylated β-catenin. SH-SY5Y cells were exposed for 6 hours to a range of concentrations of each indirubin, in the presence of MG132, and extracts were assessed in the ELISA assay. Activity was expressed as percentage of phosphorylated β-catenin in untreated control cells.
Figure 2B:
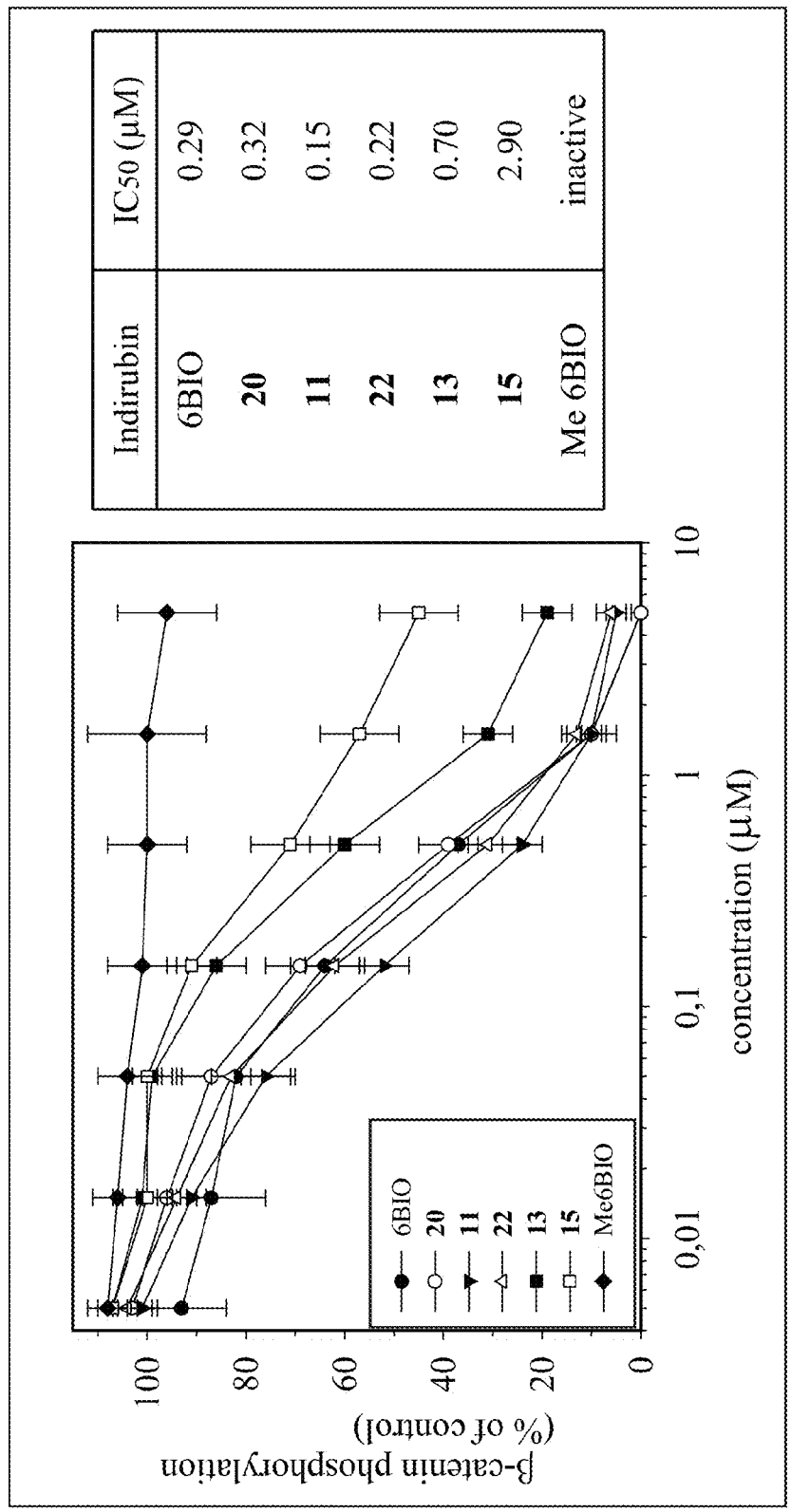

To investigate whether the new indirubins were effective at inhibiting GSK-3 in a cellular context, their effects were measured on the phosphorylation of β-catenin at GSK-3 specific sites in SH-SY5Y neuroblastoma cells. Cells were exposed to various concentrations of 10 µM of each indirubin in the presence of a constant level of MG132 (an inhibitor of the proteasome which prevented the rapid degradation of β-catenin once phosphorylated by GSK-3). The level of GSK-3-phosphorylated was estimated either by Western blotting (with an antibody that specifically cross-reacts with β-catenin when phosphorylated at a GSK-3 site) following SDS-PAGE (FIG. 2a) or by an ELISA assay (FIG. 2b). Results revealed a dose-dependent inhibition of GSK-3 selective phosphorylation sites on β-catenin, demonstrating that these compounds are actually able to inhibit GSK-3 in cells. The most efficient compounds were 6BIO, 3, 5, 9, 11, 12 and 13 (and their salts when available, i.e. 16, 20, 22, 23, 24). Dose-response curves were obtained with ELISA assay (FIG. 2b). The kinase inactive derivative 1-methyl-6BIO was ineffective in the cellular assay.

Effects on Circadian Rhythm in Mammalian Cell Cultures

Figures 3A, 3B:
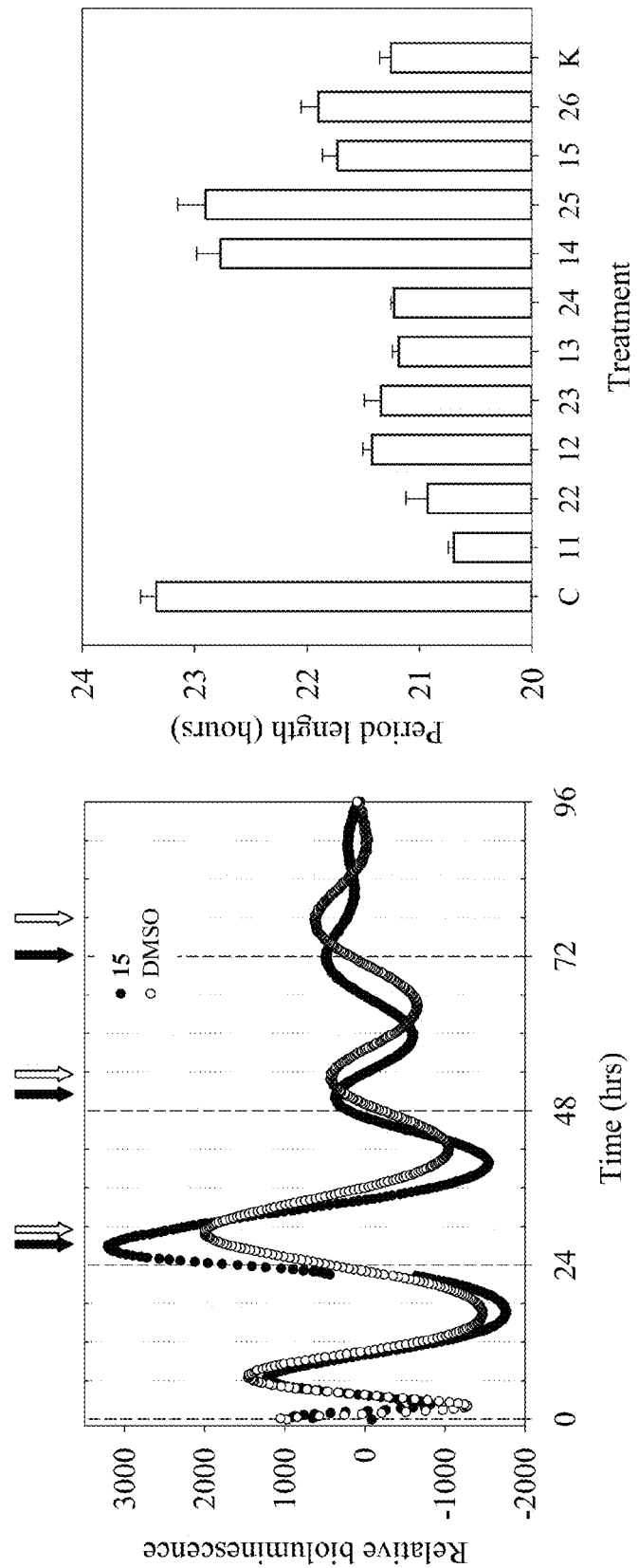
FIGS. 3a and 3b: the alteration of the circadian period in mammalian fibroblasts by the indirubin derivatives. Rat-1 fibroblasts stably transfected with a $P_{Per2}$::Fluc reporter construct show a robust circadian rhythm of luminescence as a gauge of clock-controlled Per2 promoter ($P_{Per2}$) activity. Cells were cultured up to 100% confluence and treated for 2 h with 0.1 μM dexamethasone to synchronize the oscillators. The medium was then replaced with assay medium supplemented with 0.1 mM luciferin and the luminescence rhythm was monitored for 4 days or more. Compounds were added to the culture dishes at 10 μM and left continuously. DMSO was used as a solvent control. Regression analyses were used to determine period and phase of the luminescence rhythms. 3a. Time-course of a typical luminescence rhythm recorded in control cells (○) or cells treated with indirubin 15 (•). White arrows indicate the peaks of luminescence in control cells, black arrows indicate the peaks of luminescence in indirubin 15 treated cells. 3b. Period lengths calculated in cells exposed to various compounds. C, control; K, kenpaullone.

GSK-3 is a key regulator of the circadian rhythm (aka the daily biological clock). The circadian rhythm can be partially reproduced in a cellular system which is an excellent model system for circadian clocks in non-neural, peripheral tissues. This system was used to explore the possibility that GSK-3 inhibition could affect the circadian rhythm. Rat-1 fibroblasts stably transfected with a $P_{Per2}$::Fluc reporter construct show a robust circadian rhythm of luminescence as a gauge of clock-controlled Per2 promoter ($P_{Per2}$). Cells were cultured and treated first with 10 µM indirubin 15 as described in the Experimental section and their circadian rhythm of Per expression dependent luminescence was monitored during 4 days. A gradual shortening of the period length was clearly observed (FIG. 3a). Similar experiments were next performed with a small selection of indirubins and the period length was calculated as in FIG. 3a. The most efficient compounds in shortening the period length (FIG. 3b) were also the most efficient at inhibiting β-catenin phosphorylation in the cellular assay (FIG. 2), which supports the hypothesis that the action of the indirubins in shortening the circadian period is upon GSK-3. Previous studies have suggested a key action of GSK-3 in regulating the circadian rhythms of mammalian cells using lithium as a pharmacological tool. Lithium lengthens the period of the circadian rhythm, whereas indirubins shorten the period (FIG. 5). However, the concentrations of lithium used in the previous investigations of circadian rhythms and GSK-3 were 10-20 mM, whereas the results with indirubins were obtained with concentrations 1000× lower (10 µM). These comparisons suggest that the circadian period-lengthening effects of lithium may be due to side effects of lithium. Therefore, indirubins appear to constitute a useful pharmacological tool to investigate the role of GSK-3 in the regulation of the circadian rhythm.

Through a rationale analysis of the key interactions of indirubins at the ATP-binding site of the disease-relevant glycogen synthase kinase-3, and the synthesis and biological evaluation of analogues exploring various modifications at the 3' site, we were able to uncover new interaction sites offering further stabilization to the inhibitor/GSK-3 complexes. Consequently, extensions at this site provide enhanced activity and selectivity towards GSK-3 and also provided the opportunity to introduce substitutions favoring enhanced water-solubility.

REFERENCES

1. Meijer, L; References Skaltsounis, A L; Magiatis, P; Polychonopoulos, P; Knockaert, M; Leost, M; Ryan, X P; Vonica, C D; Brivanlou, A; Dajani, R; Tarricone, A; Musacchio, A; Roe, S M; Pearl, L, Greengard, P. GSK-3 selective inhibitors derived from Tyrian purple indirubins. *Chem. & Biol.* 2003, 10, 1255-1266.
2. Jope, R. S.; Johnson, G. V. W. The glamour and gloom of glycogen synthase kinase-3. *Trends Biochem. Sci.* 2004, 29, 95-102.
3 Ribas, J.; Bettayeb, K.; Ferandin, Y.; Garrofé-Ochoa, X.; Knockaert, M.; Totzke, F.; Schächtele, C.; Mester, J.; Polychronopoulos, P.; Magiatis, P.; Skaltsounis, A. L.; Boix, J.; Meijer, L.,. 7-bromoindirubin-3'-oxime induces caspase-independent cell death. *Oncogene* 2006, 25, 6304-6318.
4 Leclerc, S.; Gamier, M.; Hoessel, R.; Marko, D.; Bibb, J. A.; Snyder, G. L.; Greengard, P.; Biernat, J.; Mandelkow, E.-M.; Eisenbrand, G.; Meijer, L. Indirubins inhibit glycogen synthase kinase-3β and CDK5/p25, two kinases involved in abnormal tau phosphorylation in Alzheimer's disease—A property common to most CDK inhibitors? *J. Biol. Chem.* 2001, 276, 251-260.
5 Primot, A.; Baratte, B.; Gompel, M.; Borgne, A.; Liabeuf, S.; Romette, J. L.; Costantini, F.; Meijer, L. Purification of GSK-3 by affinity chromatography on immobilised axin. *Protein Expr. & Purif.* 2000, 20, 394-404.
6 Ribas, J.; Boix, J. Cell differentiation, caspase inhibition, and macromolecular synthesis blockage, but not BCL-2 or BCL-XL proteins, protect SH-SY5Y cells from apoptosis triggered by two CDK inhibitory drugs. *Exp. Cell Res.* 2004, 295, 9-24.
7 Izumo, M.; Sato, T. R.; Straume M.; Johnson C. H. Quantitative analyses of circadian gene expression in mammalian cell cultures. *PLoS Computational Biology* 2006, 2, e136.

The invention claimed is:

1. An indirubin derivative of formula I

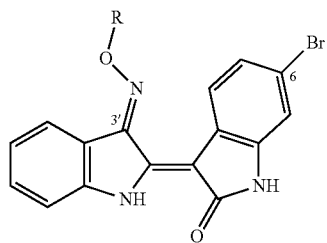

(I)

wherein
R represents $-(A)_n - R^1$ or $—CO—N(R^2,R^3)$ with
A being C1-C5 alkylene group, optionally substituted by one or several $A^1$ radical, $A^1$ being an halogen Br, OH, $OR^4$ or $NH_2$, $R^4$ being C1-C5 alkyl;
$R^1$ being halogen, OH, $N(R^2,R^3)$; $R^2$ and $R^3$, identical or different, being C1-C5 alkyl, optionally substituted by $A^1$ such as above defined, or $R^2$ and $R^3$ are part of a cycle with 5 or 6 elements optionally comprising another heteroatom such as O or N;
n=1-5,
with the exclusion of 2H-indol-2-one, 6-bromo-3-[(3E)-1,3-dihydro-3-[[2-(1-pyrrolidinyl)ethoxy]imino]-2H-indol-2-ylidene]~1,3-dihydro- , (3Z).

2. A pharmaceutically acceptable salt of an indirubin derivative of claim 1.

3. The indirubin derivative of claim 1, wherein R represents $-(A)_n-R^1$, with $R^1$ being halogen, OH, $N(R^2,R^3)$ and $R^2$ and $R^3$, identical or different, are C1-C5 alkyl, optionally substituted by $A^1$ such as above defined.

4. The indirubin derivative of claim 3, wherein $R^1$ is Br or OH and A represents a $—(CH_2)_{m1}—CH(R^1)—(CH_2)_{m2}$ radical, wherein m1=1-3 and m2=0, 1-3.

5. The indirubin derivative of claim 3, wherein $R^1$ is $N(R^2,R^3)$.

6. The indirubin derivative of claim 1, wherein A is C1-C5 alkylene group.

7. The indirubin derivative of claim 1, wherein R represents $—CO—N(R^2,R^3)$, with $R^2$ and $R^3$, identical or different, being a C1-C5 alkyl radical.

8. A pharmaceutical composition comprising a therapeutically effective amount of at least one indirubin derivative of claim 1, in association with a pharmaceutically acceptable vehicle.

9. The pharmaceutical composition of claim 8, wherein the at least one indirubin derivative is in a form suitable for an administration by intravenous route or intramuscular or subcutaneous.

* * * * *